(12) United States Patent
Nakano et al.

(10) Patent No.: US 12,324,886 B2
(45) Date of Patent: Jun. 10, 2025

(54) METHOD FOR PRODUCING BALLOON CATHETER

(71) Applicant: KANEKA CORPORATION, Osaka (JP)

(72) Inventors: Yoshinori Nakano, Settsu (JP); Yojiro Koga, Settsu (JP); Masahiro Kojima, Settsu (JP); Masato Tsueda, Settsu (JP); Shintaro Osumi, Settsu (JP)

(73) Assignee: KANEKA CORPORATION, Osaka (JP)

( * ) Notice: Subject to any disclaimer, the term of this patent is extended or adjusted under 35 U.S.C. 154(b) by 826 days.

(21) Appl. No.: 17/440,617

(22) PCT Filed: Jan. 7, 2020

(86) PCT No.: PCT/JP2020/000123
§ 371 (c)(1),
(2) Date: Sep. 17, 2021

(87) PCT Pub. No.: WO2020/194982
PCT Pub. Date: Oct. 1, 2020

(65) Prior Publication Data
US 2022/0161007 A1    May 26, 2022

(30) Foreign Application Priority Data
Mar. 22, 2019  (JP) ................................ 2019-055202

(51) Int. Cl.
*A61M 25/10*  (2013.01)
(52) U.S. Cl.
CPC ............................. *A61M 25/1029* (2013.01)

(58) Field of Classification Search
CPC ..................... A61M 25/1029; B29C 2049/222
See application file for complete search history.

(56) References Cited

U.S. PATENT DOCUMENTS

| | | | |
|---|---|---|---|
| 2003/0055378 A1* | 3/2003 | Wang | A61F 2/958 604/103.07 |
| 2005/0015107 A1 | 1/2005 | O'Brien | |
| 2007/0088378 A1 | 4/2007 | Okushi et al. | |
| 2012/0130407 A1 | 5/2012 | Aggerholm et al. | |
| 2017/0203491 A1* | 7/2017 | Vyas | B29C 49/18 |

FOREIGN PATENT DOCUMENTS

| | | | | |
|---|---|---|---|---|
| JP | 2007105332 A | * | 4/2007 | ........ A61M 25/1029 |
| JP | 2007-518448 A | | 7/2007 | |
| JP | 2014-506140 A | | 3/2014 | |

OTHER PUBLICATIONS

International Search Report for PCT/JP2020/000123 (PCT/ISA/210) mailed on Mar. 24, 2020.

* cited by examiner

*Primary Examiner* — Virak Nguon
(74) *Attorney, Agent, or Firm* — Birch, Stewart, Kolasch & Birch, LLP

(57) ABSTRACT

A method for producing a balloon catheter including preparing a balloon producing device (1), the device including a mold (10) into which a parison (50) is inserted, and a fixing member (30) for fixing the parison (50) outside the mold (10), the mold (10) provided with a rotation preventing portion (20) abutting the parison (50) so as to prevent rotation of the parison (50), disposing a part of the parison (50) in the mold (10), fixing a portion outside the mold (10) of the parison (50) with the fixing member (30), expanding the parison (50), removing the parison (50) from the mold (10), and cutting the parison (50).

16 Claims, 9 Drawing Sheets

[Fig. 1]
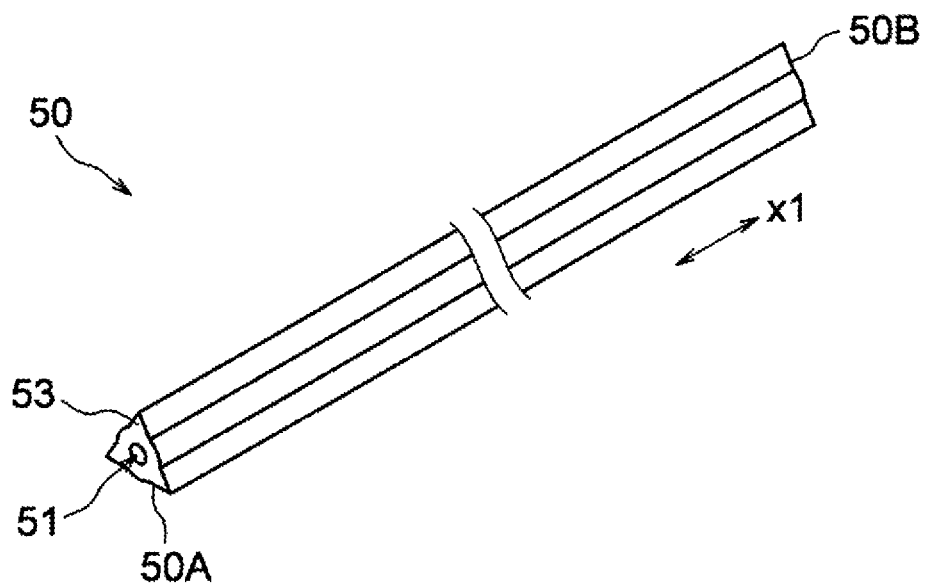
[Fig. 2]
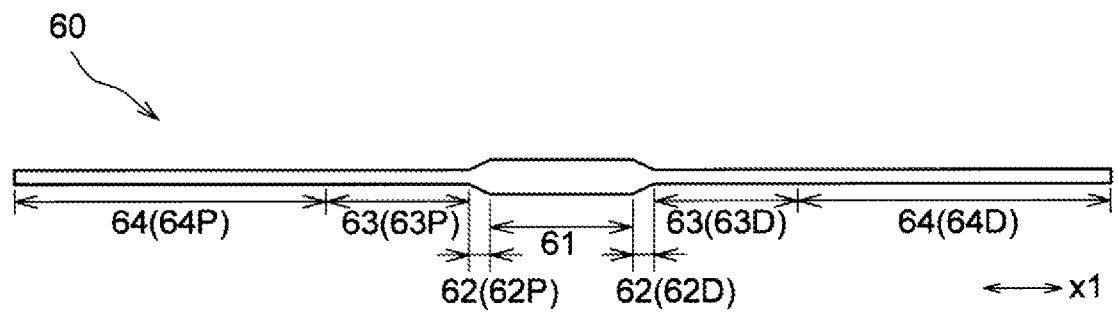

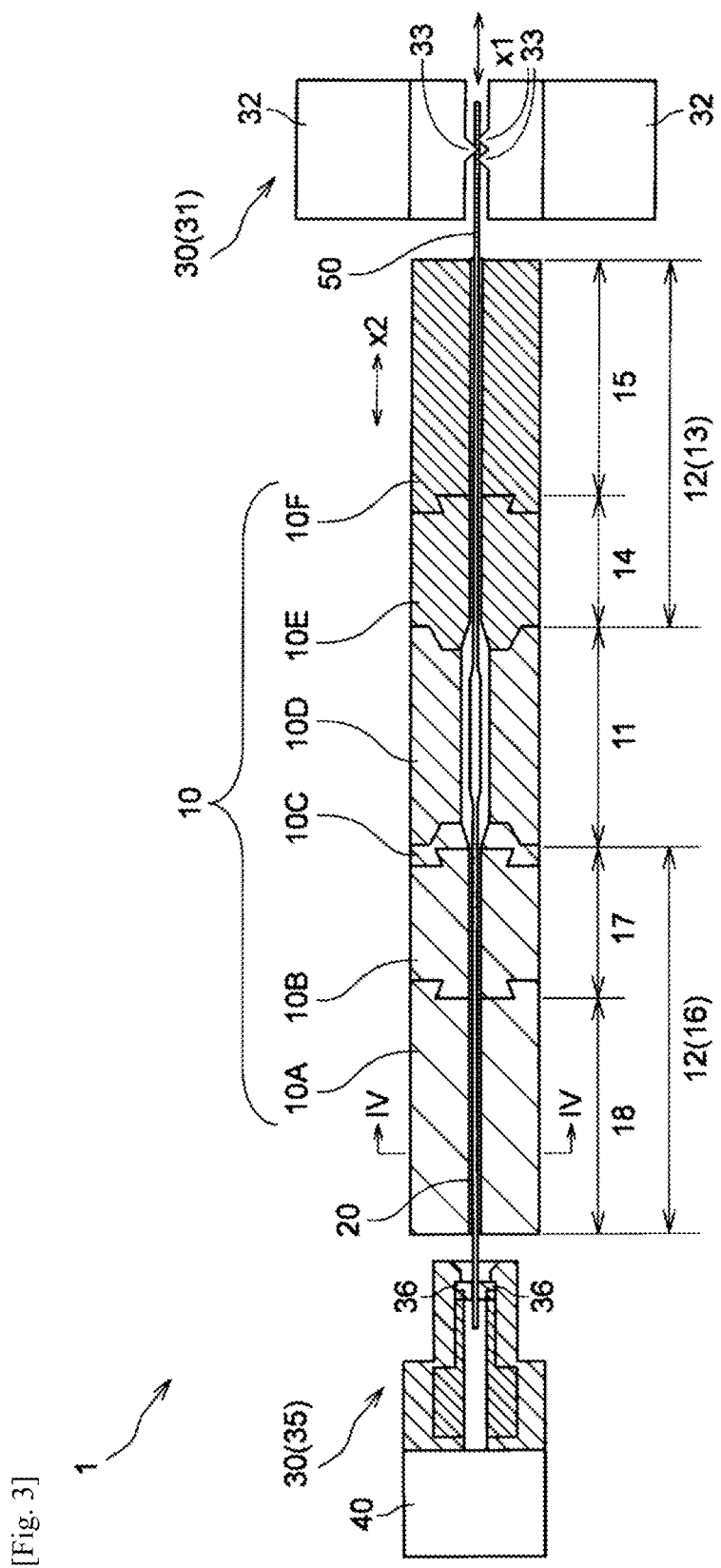

[Fig. 4]
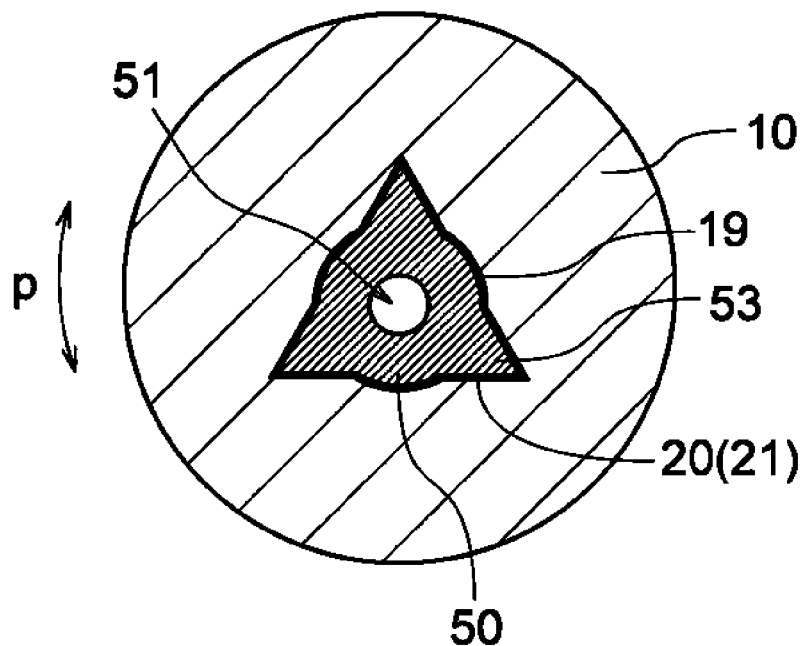
[Fig. 5]
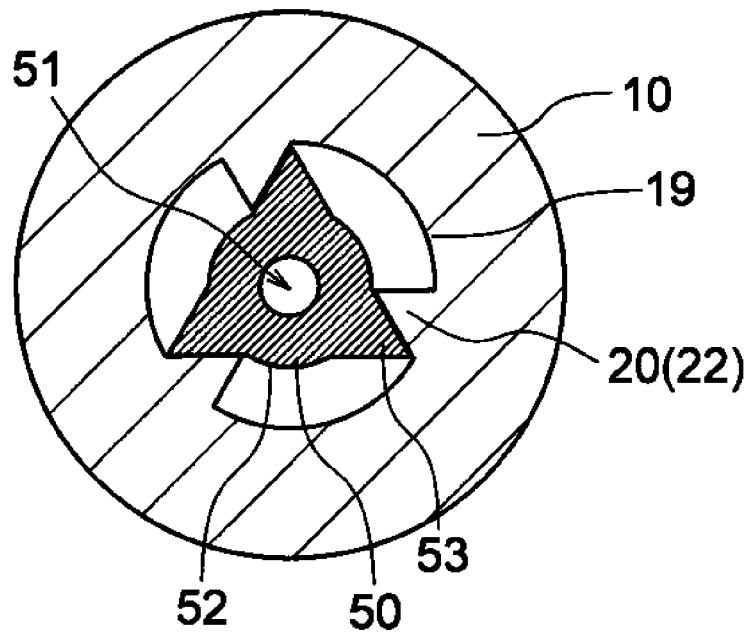

[Fig. 6]
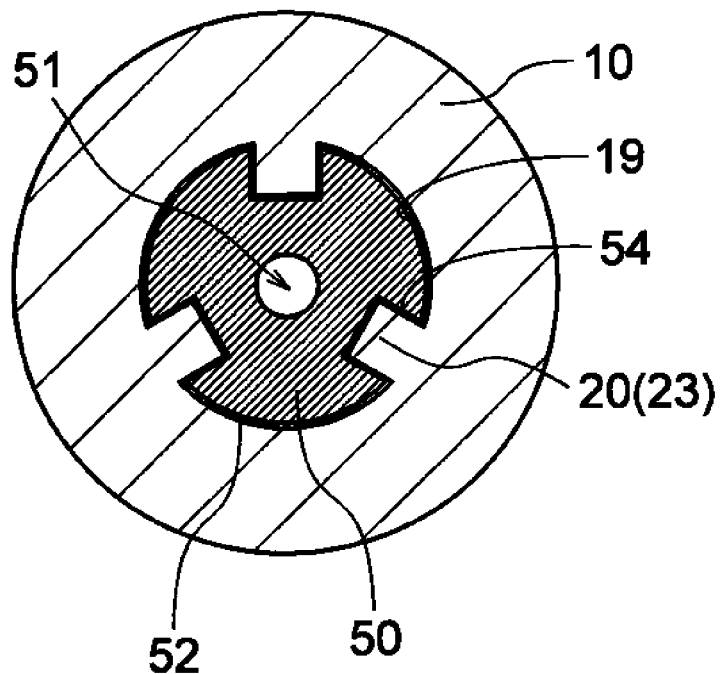
[Fig. 7]
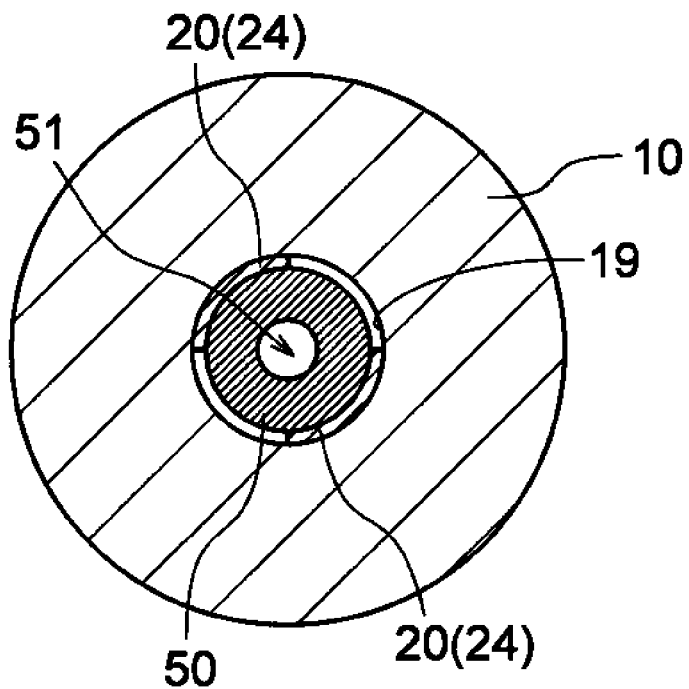

[Fig. 8]
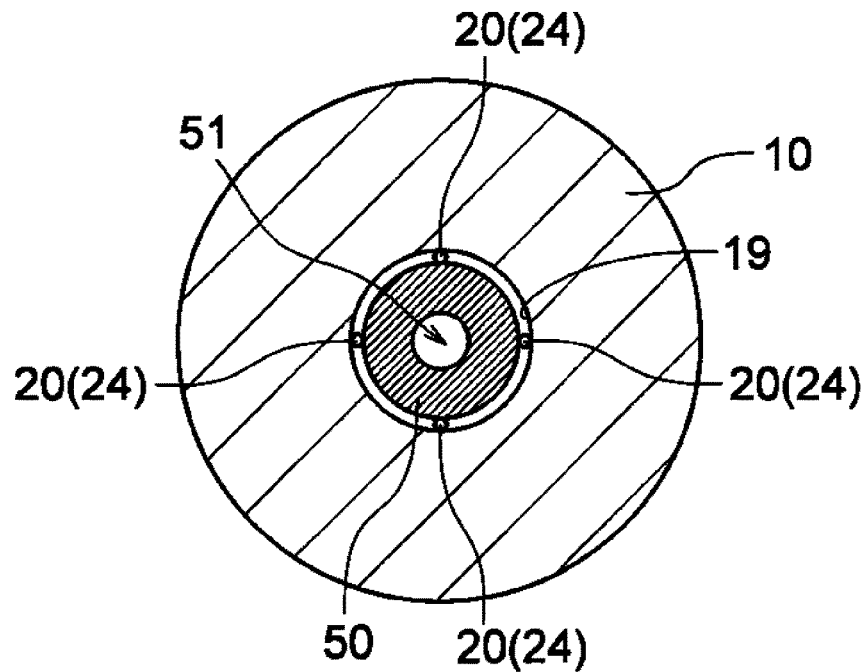
[Fig. 9]
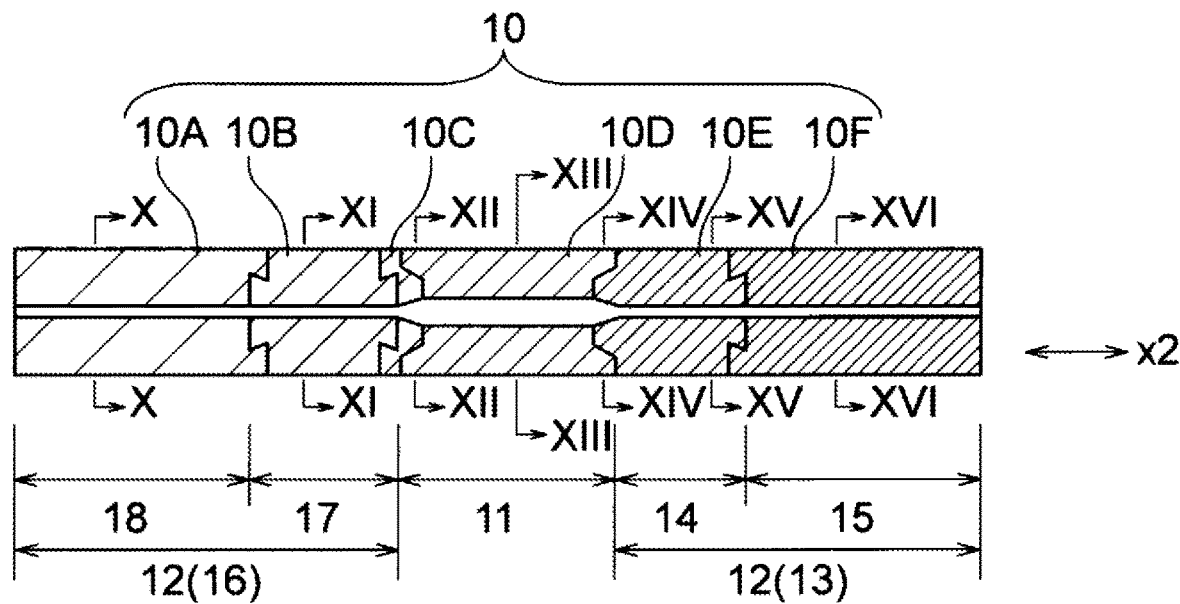

[Fig. 10]
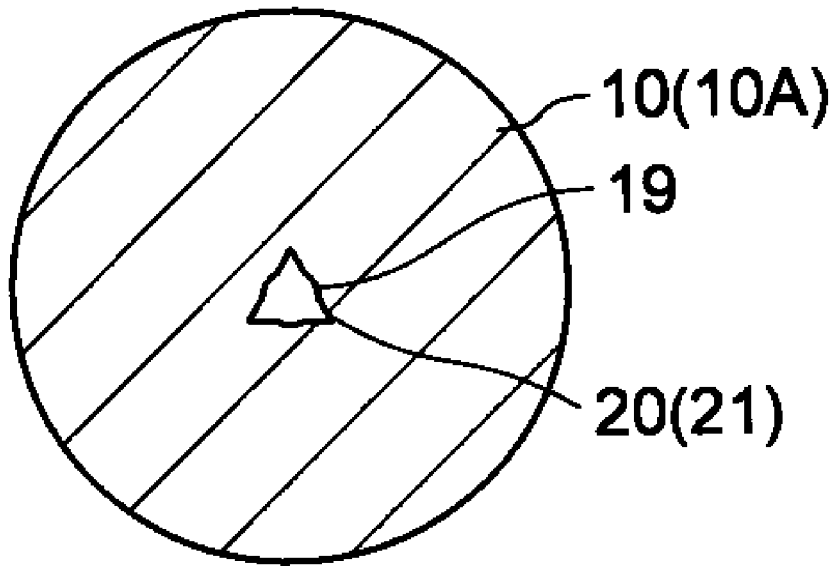
[Fig. 11]
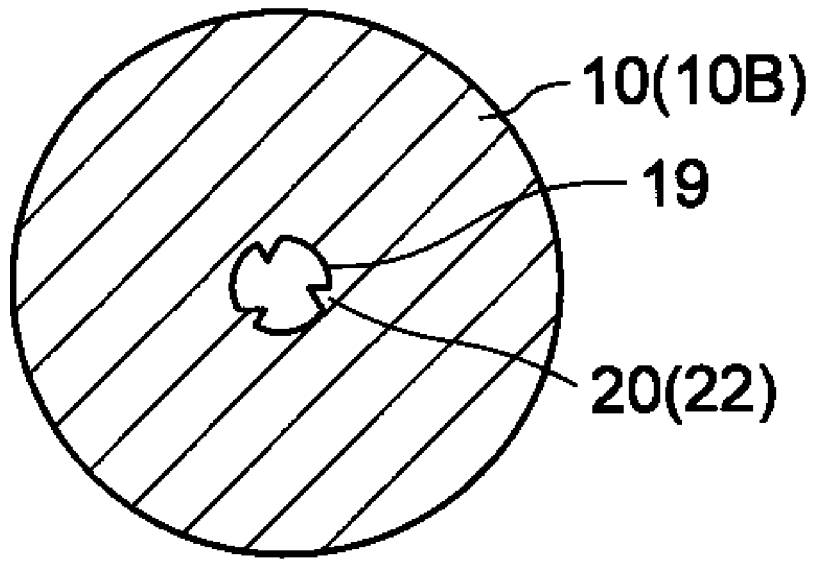

[Fig. 12]
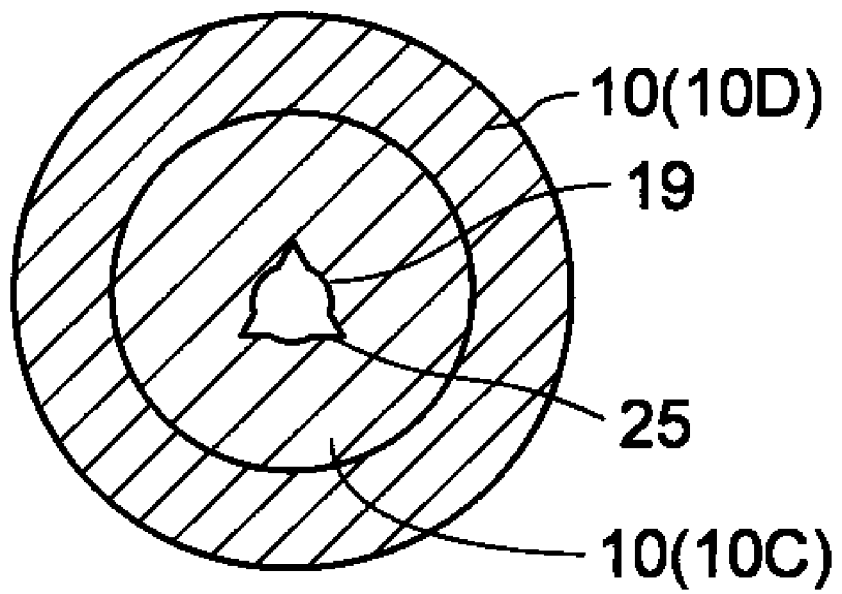
[Fig. 13]
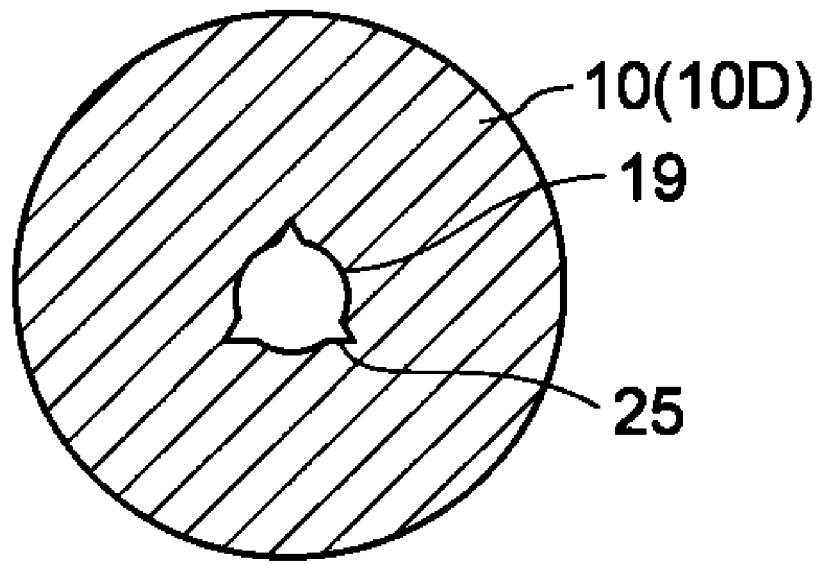

[Fig. 14]
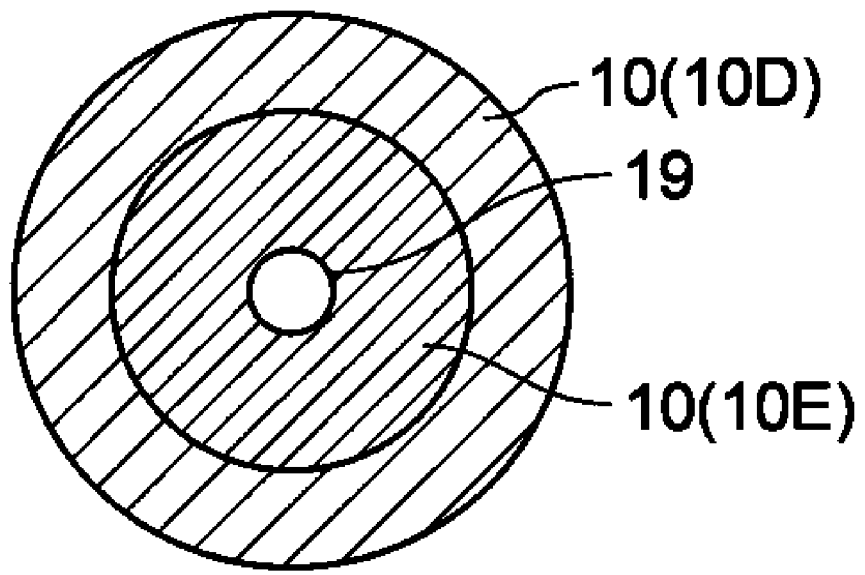
[Fig. 15]
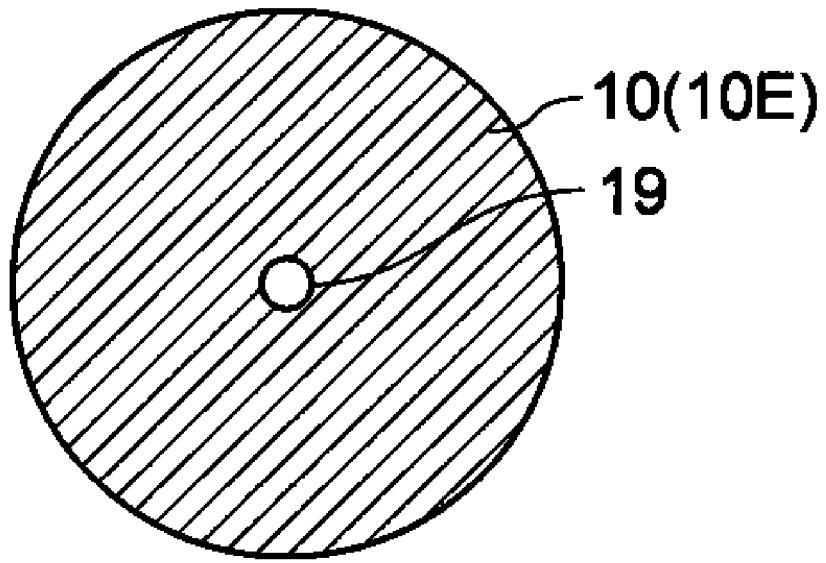

[Fig. 16]
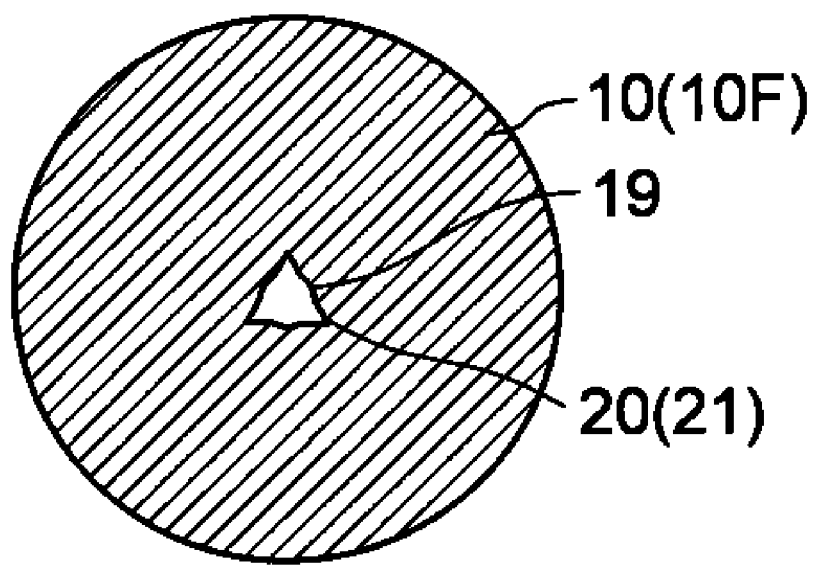

METHOD FOR PRODUCING BALLOON CATHETER

TECHNICAL FIELD

The present invention relates to a method for producing a balloon catheter using a tubular parison.

BACKGROUND ART

As disclosed in Patent Documents 1 and 2, a balloon of a balloon catheter is produced by disposing a tubular parison in a mold and expanding a lumen of the parison by blow molding.

RELATED ART DOCUMENTS

Patent Documents

Patent Document 1: JP-T-2014-506140
Patent Document 2: JP-T-2007-518448

SUMMARY OF THE INVENTION

Technical Problem

However, since the parison rotates at the time of blow molding, a problem occurs that the balloon has an irregular shape, or a projection or a recess disposed on an outer surface of the balloon is twisted in a longitudinal direction, so that a desired balloon shape cannot be obtained, and there is room for improvement. Therefore, an object of the present invention is to provide a method for producing a balloon catheter capable of preventing rotation of a parison at the time of blow molding.

Solutions to the Problems

The gist of one embodiment of a method for producing a balloon catheter according to the present invention that can overcome the above problems is as follows. The method for producing a balloon catheter includes: preparing a balloon producing device, the device including a mold into which a tubular parison is inserted, and a fixing member for fixing the parison outside the mold, the mold including a first section for forming a straight tube portion and a tapered portion of a balloon and a second section present on both sides of the first section in a longitudinal direction, the second section provided with a rotation preventing portion abutting the parison so as to prevent rotation about a longitudinal axis direction of the parison; disposing a part of the parison in the longitudinal axis direction in the mold; fixing a portion disposed outside the mold of the parison with the fixing member; expanding the parison; removing the parison from the mold; and cutting the parison at a position corresponding to the second section. According to the present invention, the rotation of the parison may be prevented at a step of expanding the parison by a fixing member for fixing the parison outside a mold and a rotation preventing portion provided in the mold. Therefore, it is possible to produce a balloon and a projection and a recess disposed on an outer surface thereof into a desired shape.

Preferably, the rotation preventing portion is disposed in each of a distal second section present at a position corresponding to a distal side of the balloon with respect to the first section out of the second section and a proximal second section present at a position corresponding to a proximal side of the balloon with respect to the first section out of the second section.

Preferably, in the expanding the parison, a pressurizing member for introducing a fluid into the parison is connected to a first side or a second side in the longitudinal axis direction of the parison, and the rotation preventing portion is disposed in any one of a distal second section present at a position corresponding to a distal side of the balloon with respect to the first section and a proximal second section present at a position corresponding to a proximal side of the balloon with respect to the first section out of the second section, the section on the side on which the pressurizing member is connected to the parison.

Preferably, the fixing member includes a first fixing member for fixing a first side in the longitudinal axis direction of the parison, and a second fixing member for fixing a second side in the longitudinal axis direction of the parison, at least any one of the first fixing member and the second fixing member is movable in the longitudinal axis direction of the parison, and the rotation preventing portion is disposed in any one of a distal second section present at a position corresponding to a distal side of the balloon with respect to the first section and a proximal second section present at a position corresponding to a proximal side of the balloon with respect to the first section out of the second section, the section in which either the first fixing member or the second fixing member having a longer distance to move in the longitudinal axis direction of the parison is disposed.

Preferably, the fixing member includes the first fixing member for fixing a first side in the longitudinal axis direction of the parison and the second fixing member for fixing a second side in the longitudinal axis direction of the parison, and in the fixing a portion disposed outside the mold of the parison with the fixing member, the first fixing member fixes in such a way that a lumen cross-sectional shape of the parison is deformed as compared with the shape before fixing, and the second fixing member fixes in such a way that a deformation amount of the lumen cross-sectional shape of the parison is less than the deformation amount when fixing with the first fixing member.

Preferably, in the cutting the parison at a position corresponding to the second section, the parison is cut on a side of the straight tube portion with respect to a portion abutting the rotation preventing portion.

Preferably, in the cutting the parison at a position corresponding to the second section, the parison is cut at positions corresponding to the distal second section present at the position corresponding to the distal side of the balloon with respect to the first section and the proximal second section present at the position corresponding to the proximal side of the balloon with respect to the first section out of the second section.

Preferably, a first projection is disposed on an outer surface of the parison, and the rotation preventing portion is a first groove disposed on an inner wall surface of the mold and engaging with the first projection, or a second projection disposed on the inner wall surface of the mold and abutting the first projection.

Preferably, the first projection extends in the longitudinal axis direction of the parison, and the first groove or the second projection extends in the longitudinal direction of the mold.

Preferably, a first recess is disposed on an outer surface of the parison, and the rotation preventing portion is a third projection disposed on an inner wall surface of the mold and engaging with the first recess.

Preferably, the rotation preventing portion is an inner wall surface of the second section of the mold having surface roughness more than surface roughness of an inner wall surface of the first section of the mold, or an outer surface of the parison at the position corresponding to the second section having surface roughness more than surface roughness of the outer surface of the parison at a position corresponding to the first section. The surface roughness is arithmetic average roughness Ra in a reference length of a roughness curve on the inner wall surface of the mold or the outer surface of the parison, and the reference length is 0.1 mm.

Preferably, the rotation preventing portion is a first frictional resistance member provided on the inner wall surface of the second section and having frictional resistance more than frictional resistance of the inner wall surface of the first section, or a second frictional resistance member provided on an outer surface of the parison at the position corresponding to the second section and having frictional resistance more than frictional resistance of the outer surface of the parison at a position corresponding to the first section.

Preferably, out of the second section, the distal second section present at the position corresponding to the distal side of the balloon with respect to the first section includes a distal 2-1 section present on a side of the first section for forming a distal sleeve portion of the balloon, and a distal 2-2 section present at a position corresponding to a distal side of the balloon with respect to the distal 2-1 section, out of the second section, the proximal second section present at the position corresponding to the proximal side of the balloon with respect to the first section includes a proximal 2-1 section present on a side of the first section for forming a proximal sleeve portion of the balloon, and a proximal 2-2 section present at a position corresponding to a proximal side of the balloon with respect to the proximal 2-1 section, and the rotation preventing portion is disposed in at least any one of the distal 2-1 section and the proximal 2-1 section, the distal 2-2 section, and the proximal 2-2 section.

Preferably, the rotation preventing portion is disposed in the distal 2-2 section, the proximal 2-1 section, and the proximal 2-2 section, and is not disposed in the distal 2-1 section.

Preferably, in the expanding the parison, a pressurizing member for introducing a fluid into the parison is connected to a first side or a second side in the longitudinal axis direction of the parison, and the rotation preventing portion is disposed in any one of the distal 2-1 section and the proximal 2-1 section, the section on the side on which the pressurizing member is connected to the parison, the distal 2-2 section, and the proximal 2-2 section.

Preferably, the fixing member includes a first fixing member for fixing a first side in the longitudinal axis direction of the parison, and a second fixing member for fixing a second side in the longitudinal axis direction of the parison, at least any one of the first fixing member and the second fixing member is movable in the longitudinal axis direction of the parison, and the rotation preventing portion is disposed in any one of the distal 2-1 section and the proximal 2-1 section, the section in which either the first fixing member or the second fixing member having a longer distance to move in the longitudinal axis direction of the parison is disposed, the distal 2-2 section, and the proximal 2-2 section.

Advantageous Effects of the Invention

According to the method for producing, the rotation of the parison may be prevented at a step of expanding the parison. Therefore, it is possible to produce a balloon and a projection and a recess disposed on an outer surface thereof into a desired shape.

BRIEF DESCRIPTION OF THE DRAWINGS

FIG. 1 is a perspective view of a parison according to one embodiment of the present invention.

FIG. 2 is a side view of a balloon according to one embodiment of the present invention.

FIG. 3 is a cross-sectional view (partial side view) of a balloon producing device according to one embodiment of the present invention.

FIG. 4 is a cross-sectional view taken along line IV-IV of the balloon producing device illustrated in FIG. 3, and FIG. 4 illustrates an arrangement example of a rotation preventing portion of the mold and a parison.

FIG. 5 is a cross-sectional view according to a modification example of the balloon producing device illustrated in FIG. 4.

FIG. 6 is a cross-sectional view according to another modification example of the balloon producing device illustrated in FIG. 4.

FIG. 7 is a cross-sectional view according to still another modification example of the balloon producing device illustrated in FIG. 4.

FIG. 8 is a cross-sectional view according to still another modification example of the balloon producing device illustrated in FIG. 4.

FIG. 9 is a cross-sectional view of a mold according to another embodiment of the present invention.

FIG. 10 is a cross-sectional view taken along line X-X of the mold illustrated in FIG. 9.

FIG. 11 is a cross-sectional view taken along line XI-XI of the mold illustrated in FIG. 9.

FIG. 12 is a cross-sectional view taken along line XII-XII of the mold illustrated in FIG. 9.

FIG. 13 is a cross-sectional view taken along line XIII-XIII of the mold illustrated in FIG. 9.

FIG. 14 is a cross-sectional view taken along line XIV-XIV of the mold illustrated in FIG. 9.

FIG. 15 is a cross-sectional view taken along line XV-XV of the mold illustrated in FIG. 9.

FIG. 16 is a cross-sectional view taken along line XVI-XVI of the mold illustrated in FIG. 9.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

One embodiment of a method for producing a balloon catheter according to the present invention includes: preparing a balloon producing device, the device including a mold into which a tubular parison is inserted, and a fixing member for fixing the parison outside the mold, the mold including a first section for forming a straight tube portion and a tapered portion of a balloon and a second section present on both sides of the first section in a longitudinal direction, the second section provided with a rotation preventing portion abutting the parison so as to prevent rotation about a longitudinal axis direction of the parison; disposing a part of the parison in the longitudinal axis direction in the mold; fixing a portion disposed outside the mold of the parison with the fixing member; expanding the parison; removing the parison from the mold; and cutting the parison at a position corresponding to the second section. According to the present invention, the rotation of the parison may be prevented at a step of expanding the parison by a fixing member for fixing the parison outside a mold and a rotation preventing portion provided in the mold. Therefore, it is possible to produce a balloon and a projection and a recess disposed on an outer surface thereof into a desired shape.

A parison and a balloon producing device used in the above-described producing method are described with reference to FIGS. 1 to 4. FIG. 1 is a perspective view of a parison according to one embodiment of the present invention, and FIG. 2 is a side view of a balloon according to one embodiment of the present invention. FIG. 3 is a cross-sectional view (partial side view) of a balloon producing device according to one embodiment of the present invention, and FIG. 4 is a cross-sectional view taken along line Iv-Iv of the balloon producing device illustrated in FIG. 3. Note that, FIG. 3 illustrates a state in which a parison 50 before expansion is disposed in a mold 10.

A balloon catheter is a medical instrument used in angioplasty (PTA, PTCA and the like) for dilating a stenosis part performed mainly in treatment of the stenosis part of the blood vessel. It is known that various diseases occur when the blood vessel, which is a flow path for circulating blood in a body, becomes stenosed and blood circulation becomes sluggish. Especially when the coronary artery that supplies blood to the heart becomes stenosed, this might cause severe diseases such as angina pectoris and myocardial infarction. Angioplasty is widely performed because this is minimally invasive therapy that does not require thoracotomy such as bypass surgery.

The balloon catheter includes a shaft and a balloon provided outside the shaft. The balloon catheter has a proximal side and a distal side, the balloon is provided on a distal side of the shaft, and a hub is provided on a proximal side of the shaft. Note that a proximal side of the balloon refers to a side near a user (operator) in an extending direction of the balloon catheter, and a distal side refers to a side in a direction opposite to the proximal side (that is, a direction toward a treated target).

As illustrated in FIG. 1, the parison 50 is a tubular resin mass fabricated by extrusion molding. The parison 50 includes a first end 50A and a second end 50B, and extends in a longitudinal axis direction x1 from the first end 50A toward the second end 50B. As illustrated in FIG. 3, when the parison 50 is disposed in the mold 10, at least any one of a first side and a second side in the longitudinal axis direction x1 is exposed from the mold 10. It is especially preferable that the first side and the second side of the parison 50 in the longitudinal axis direction x1 are exposed from the mold 10. The balloon for the balloon catheter may be produced by introducing a fluid such as air, nitrogen, or water into a lumen 51 of the parison 50 and expanding the parison 50.

FIG. 2 illustrates a balloon 60 formed by expanding the parison 50. The balloon 60 includes a straight tube portion 61, a tapered portion 62 disposed on both sides of the straight tube portion 61 with an outer diameter decreasing toward an end side in the longitudinal axis direction x1, a sleeve portion 63 disposed on the end side in the longitudinal axis direction x1 with respect to the tapered portion 62 and connected to the shaft of the balloon catheter, and a sleeve outer portion 64 disposed on the end side in the longitudinal axis direction x1 with respect to the sleeve portion 63 and cut at a step described later. Since the sleeve outer portion 64 is an unnecessary portion as a final product, this is cut. The tapered portion 62 disposed on the distal side with respect to the straight tube portion 61 is referred to as a distal tapered portion 62D, and the tapered portion 62 disposed on the proximal side with respect to the straight tube portion 61 is referred to as a proximal tapered portion 62P. The sleeve portion 63 disposed on the distal side with respect to the distal tapered portion 62D is referred to as a distal sleeve portion 63D, and the sleeve portion 63 disposed on the proximal side with respect to the proximal tapered portion 62P is referred to as a proximal sleeve portion 63P. Furthermore, the sleeve outer portion 64 disposed on the distal side with respect to the distal sleeve portion 63D is referred to as a distal sleeve outer portion 64D, and the sleeve outer portion 64 disposed on the proximal side with respect to the proximal sleeve portion 63P is referred to as a proximal sleeve outer portion 64P.

A first projection 53 (refer to FIG. 1) projecting radially outward or a recess (not illustrated) recessed radially inward may be disposed on the outer surface of the parison 50. At least a part of the projection or recess preferably remains on the outer surface of the balloon 60 even after a step of expanding the parison 50.

As illustrated in FIG. 1, a cross-sectional shape of the parison 50 in a direction perpendicular to the longitudinal axis direction x1 may be substantially uniform in the longitudinal axis direction x1. Accordingly, productivity of the parison 50 may be enhanced. The cross-sectional shape of the parison 50 in the direction perpendicular to the longitudinal axis direction x1 may differ depending on a position in the longitudinal axis direction x1. In FIG. 3, an outer diameter of a part (for example, a portion corresponding to the straight tube portion of the balloon) of the parison 50 in the longitudinal axis direction x1 is larger than that of a part other than this part. In order to make the cross-sectional shape of the parison differ in the longitudinal axis direction x1 in this manner, blow molding may be performed using another mold in advance.

Examples of a material forming the parison 50 include, for example, a polyolefin-based resin such as polyethylene, polypropylene, and an ethylene-propylene copolymer, a polyester-based resin such as polyethylene terephthalate and polyester elastomer, a polyurethane-based resin such as polyurethane and polyurethane elastomer, a polyphenylene-sulfide-based resin, a polyamide-based resin such as polyamide and polyamide elastomer, a fluorine-based resin, a silicone-based resin, and natural rubber such as latex rubber. It is possible to use only one of them or two or more of them. Among them, the polyamide-based resin, polyester-based resin, and polyurethane-based resin are suitably used. It is especially preferable to use an elastomer resin from the viewpoint of thinning and flexibility of the balloon. For example, examples of a material suitable for the parison 50 among the polyamide-based resins include nylon 12, nylon 11 and the like, and nylon 12 is suitably used because this may be relatively easily molded at the time of blow molding. From the viewpoint of thinning and flexibility of the balloon, polyamide elastomer such as polyether ester amide elastomer and polyamide ether elastomer are preferably used. Among them, polyether ester amide elastomer is preferably used from the viewpoint of high yield strength and excellent dimensional stability of the balloon.

The balloon producing device 1 includes the mold 10 and a fixing member 30. The parison 50 is inserted into the mold 10. Specifically, a part of the parison 50 in the longitudinal axis direction x1 is disposed in the mold 10. As illustrated in FIG. 3, the mold 10 has a longitudinal direction x2 corresponding to the longitudinal axis direction x1 of the parison 50. In order to easily dispose the parison 50 in the mold 10, the longitudinal direction x2 of the mold 10 preferably coincides with the longitudinal axis direction x1 of the parison 50. The mold 10 includes a first section 11 for forming the straight tube portion 61 and the tapered portion 62 of the balloon 60, and a second section 12 present on both sides of the first section 11 in the longitudinal direction x2. Out of the parison 50, a portion corresponding to the first section 11 of the mold 10 forms the straight tube portion 61 and the tapered portion 62 of the balloon 60, and a portion corresponding to the second section 12 of the mold 10 forms the sleeve portion 63 and the sleeve outer portion 64 of the balloon 60.

The mold 10 may be formed of one member or may be formed of a plurality of members. For example, the mold 10 may be formed of a plurality of half-cut bodies, or a plurality of mold members may be connected to each other in the longitudinal direction x2. It is especially preferable that the mold 10 is formed of a plurality of mold members having different lumen cross-sectional shapes. In FIG. 3, the mold 10 includes a first mold 10A, a second mold 10B, a third mold 10C, a fourth mold 10D, a fifth mold 10E, and a sixth mold 10F in this order from the proximal side. As illustrated in FIG. 3, adjacent metal mold members may be engaged with each other to be connected. Although not illustrated, magnets may be attached to each of the adjacent mold members, and they may attract each other to be connected.

The lumen cross-sectional shape of the mold 10 may have a circular shape, an elliptical shape, a polygonal shape, or a shape obtained by combining these shapes.

The fixing member 30 fixes the parison 50 outside the mold 10. By fixing a portion disposed outside the mold 10 out of the parison 50 with the fixing member 30, it is possible to prevent rotation of the parison 50 at the step of expanding the parison 50. It is preferable that the parison 50 fixed by the fixing member 30 cannot rotate and cannot move in the longitudinal axis direction x1.

The fixing member 30 preferably fixes at least one side in the longitudinal axis direction x1 of the parison 50, and more preferably includes a first fixing member 31 for fixing the first side in the longitudinal axis direction x1 of the parison 50 and a second fixing member 35 for fixing the second side in the longitudinal axis direction x1 of the parison 50 as illustrated in FIG. 3. Accordingly, it is difficult for the parison 50 to rotate even when the parison 50 is expanded. A fixing position of the parison 50 is not especially limited, but it is preferable to fix a range within 10 cm from the first end 50A or the second end 50B in the longitudinal axis direction x1 of the parison 50, and it is more preferable to fix a range within 8 cm, and still more preferable to fix a range within 5 cm. A fixing mechanism of the first fixing member 31 and that of the second fixing member 35 may be the same as or different from each other.

The fixing member 30 preferably fixes a position corresponding to the sleeve outer portion 64 of the balloon 60 out of the parison 50. The sleeve outer portion 64 of the balloon 60 is a portion that is cut off before being fixed to the shaft and is not used as the final product. Therefore, by fixing the sleeve outer portion 64 with the fixing member 30, an influence on a shape and a quality of a product balloon may be eliminated.

The fixing member 30 includes a plurality of chuck pieces, and may grip the parison 50 by the plurality of chuck pieces. It is also possible that the fixing member 30 includes fastening members facing each other and fastens to fix the parison 50 by these fastening members.

Note that, in FIG. 3, the first fixing member 31 that includes two fastening members 32 facing each other and fastens to fix a distal end of the parison 50 by the fastening members 32, and the second fixing member 35 that includes two chuck pieces 36 and grips a proximal end of the parison 50 by the chuck pieces 36 are illustrated. The fastening members 32 include teeth 33 that mesh with each other.

It is preferable that at least any one of the first fixing member 31 and the second fixing member 35 is movable in the longitudinal axis direction x1 of the parison 50. When at least any one of the first fixing member 31 and the second fixing member 35 moves, the parison 50 may be extended in the longitudinal axis direction x1.

In a case where the fixing member 30 includes the first fixing member 31 for fixing the first side in the longitudinal axis direction x1 of the parison 50 and the second fixing member 35 for fixing the second side in the longitudinal axis direction x1 of the parison 50, at a step of fixing a portion disposed outside the mold 10 of the parison 50 with the fixing member 30, the first fixing member 31 preferably fixes in such a way that a lumen cross-sectional shape of the parison 50 is deformed as compared with the shape before fixing, and the second fixing member 35 preferably fixes in such a way that a deformation amount of the lumen cross-sectional shape of the parison 50 is less than that when fixing with the first fixing member 31. Accordingly, the parison 50 may be fixed in a state in which the lumen 51 of the parison 50 is secured by the second fixing member 35, that is, in a state in which the lumen 51 of the parison 50 is not completely crushed, and the fluid may be introduced thereinto, so that the step of expanding the parison 50 may be efficiently performed.

As illustrated in FIG. 3, the second section 12 of the mold 10 is provided with a rotation preventing portion 20 that abuts the parison 50 so as to prevent rotation of the parison 50 about the longitudinal axis direction x1. The rotation preventing portion 20 includes a portion that locks the parison 50 or a portion that generates frictional resistance between the same and the parison 50, and is formed on an inner wall surface 19 of the mold 10. By providing the rotation preventing portion 20 in addition to the fixing member 30 in this manner, the parison 50 abuts the rotation preventing portion 20 at the step of expanding the parison 50, so that the rotation of the parison 50 may be further prevented.

One or a plurality of the rotation preventing portions 20 may be provided in the mold 10; it is preferable to provide a plurality of them in order to enhance a rotation preventing effect of the parison 50.

In the rotation preventing portion 20, the parison 50 is preferably not fixed with respect to the mold 10 in the longitudinal direction x2. That is, the parison 50 preferably moves in the longitudinal direction x2 with respect to the mold 10. Accordingly, the parison 50 is easily inserted into the mold 10.

The rotation preventing portion 20 may be provided, for example, in a position hereinafter described.

The rotation preventing portion 20 is preferably disposed in either a distal second section 13 present at a position corresponding to the distal side of the balloon with respect to the first section 11 out of the second section 12 (hereinafter, simply referred to as a "distal second section") or a proximal second section 16 present at a position corresponding to the proximal side of the balloon with respect to the first section 11 out of the second section 12 (hereinafter, simply referred to as a "proximal second section"). By providing one rotation preventing portion 20 in this manner, the rotation preventing effect of the parison 50 may be obtained.

The rotation preventing portion 20 is preferably disposed in each of the distal second section 13 and the proximal second section 16. By disposing the rotation preventing portion 20 in each of the distal second section 13 and the proximal second section 16, the rotation preventing effect of the parison 50 may be further enhanced.

At the step of expanding the parison 50, a pressurizing member 40 for introducing a fluid into the parison 50 is preferably connected to the first side or the second side in the longitudinal axis direction x1 of the parison 50. Accordingly, it becomes possible to expand the parison 50 to mold the balloon. In FIG. 3, the pressurizing member 40 is connected to the proximal end of the parison 50 in the longitudinal axis direction x1 via the second fixing member 35, but the pressurizing member 40 may also be connected to the distal end of the parison 50 in the longitudinal axis direction x1.

In a case where the fixing member 30 includes the first fixing member 31 and the second fixing member 35, the first fixing member 31 fixes in such a way that a lumen cross-sectional shape of the parison 50 is deformed as compared with that before fixing, and the second fixing member 35 fixes in such a say that a deformation amount of the lumen cross-sectional shape of the parison 50 is less than that when fixing with the first fixing member 31, it is preferable that the pressurizing member 40 is disposed on the first side or the second side in the longitudinal axis direction x1 of the parison 50, the side of the second fixing member 35. Accordingly, it becomes possible to introduce the fluid into the parison 50 from the side of the second fixing member 35 while narrowing the lumen 51 of the parison 50 by the first fixing member 31.

In a case where the pressurizing member 40 is connected to the first side or the second side in the longitudinal axis direction x1 of the parison 50, the rotation preventing portion 20 is preferably disposed in any one of the distal second section 13 and the proximal second section 16, the section on the side on which the pressurizing member 40 is connected to the parison 50. On the side of the parison 50 to which the pressurizing member 40 is connected, rotation and positional displacement of the parison 50 are more likely to occur as compared to the side to which the pressurizing member 40 is not connected due to a reaction force at the time of fluid introduction into the lumen 51 of the parison 50. Therefore, the rotation of the parison 50 may be efficiently prevented by providing the rotation preventing portion 20 in either the distal second section 13 or the proximal second section 16, the section on the side on which the pressurizing member 40 is connected to the parison 50.

The fixing member 30 includes the first fixing member 31 that fixes the first side in the longitudinal axis direction x1 of the parison 50 and the second fixing member 35 that fixes the second side in the longitudinal axis direction x1 of the parison 50, and at least any one of the first fixing member 31 and the second fixing member 35 is movable in the longitudinal axis direction x1 of the parison 50. In this case, the rotation preventing portion 20 is preferably disposed in any one of the distal second section 13 and the proximal second section 16 in which either the first fixing member 31 or the second fixing member 35 having a longer distance to move in the longitudinal axis direction x1 of the parison 50 is disposed. On the side in the longitudinal axis direction x1 of the parison 50 on which the fixing member 30 having the longer distance to move is disposed, rotational deviation due to extension of the parison 50 at the time of blow molding is likely to occur as compared to the side on which the fixing member 30 having a shorter distance to move is disposed. Therefore, the rotation of the parison 50 may be efficiently prevented by providing the rotation preventing portion 20 at the above-described position.

The distal second section 13 may include a distal 2-1 section 14 present on a side of the first section 11 for forming the distal sleeve portion 63D of the balloon, and a distal 2-2 section 15 present at a position corresponding to the distal side of the balloon with respect to the distal 2-1 section 14. The proximal second section 16 may include a proximal 2-1 section 17 present on a side of the first section 11 for forming the proximal sleeve portion 63P of the balloon, and a proximal 2-2 section 18 present at a position corresponding to the proximal side of the balloon with respect to the proximal 2-1 section 17.

In a case where the distal second section 13 includes the distal 2-1 section 14 and the distal 2-2 section 15, and the proximal second section 16 includes the proximal 2-1 section 17 and the proximal 2-2 section 18, it is preferable that the rotation preventing portion 20 is disposed in the distal 2-2 section 15 and the proximal 2-2 section 18, and is not disposed in the distal 2-1 section 14 and the proximal 2-1 section 17. Portions corresponding to the distal 2-2 section 15 and the proximal 2-2 section 18 of the parison 50 are at positions corresponding to an outer side of the sleeve portion 63 of the balloon 60 (that is, the sleeve outer portion 64 of the balloon 60), so that they are portions that are cut off before being fixed to the shaft and are not used as the final product. By disposing the rotation preventing portion 20 in the sections, an influence on the shape and quality of the product balloon may be eliminated.

In a case where the distal second section 13 includes the distal 2-1 section 14 and the distal 2-2 section 15, and the proximal second section 16 includes the proximal 2-1 section 17 and the proximal 2-2 section 18, it is preferable that the rotation preventing portion 20 is disposed in at least any one of the distal 2-1 section 14 and the proximal 2-1 section 17, and in the distal 2-2 section 15 and the proximal 2-2 section 18. By providing the rotation preventing portion 20 in the distal 2-2 section 15 and the proximal 2-2 section 18, an influence on the shape and quality of the product balloon may be eliminated. By disposing the rotation preventing portion 20 also in at least any one of the distal 2-1 section 14 and the proximal 2-1 section 17, the rotation preventing effect of the parison 50 is enhanced.

In the longitudinal direction x2 of the mold 10, the distal 2-2 section 15 is preferably longer than the distal 2-1 section 14. Accordingly, the rotation preventing portion 20 of the mold 10 easily abuts the parison 50 in a wide range. For a similar reason, in the longitudinal direction x2 of the mold 10, the proximal 2-2 section 18 is preferably longer than the proximal 2-1 section 17.

It is preferable that the rotation preventing portion 20 is disposed in the distal 2-2 section 15, the proximal 2-1 section 17, and the proximal 2-2 section 18, and is not disposed in the distal 2-1 section 14. By not disposing the rotation preventing portion 20 in the distal 2-1 section 14 for forming the distal sleeve portion 63D of the balloon 60, slipperiness of the distal sleeve portion 63D of the balloon 60 is appropriately secured, so that crossability of the balloon at a lesion may be enhanced.

At the step of expanding the parison 50, it is preferable that the pressurizing member 40 for introducing the fluid into the parison 50 is connected to the first side or the second side in the longitudinal axis direction x1 of the parison 50, and the rotation preventing portion 20 is disposed in any one of the distal 2-1 section 14 and the proximal 2-1 section 17, the section on the side on which the pressurizing member 40 is connected to the parison 50, the distal 2-2 section 15, and the proximal 2-2 section 18. By providing the rotation preventing portion 20 in the distal 2-2 section 15 and the proximal 2-2 section 18, an influence on the shape and quality of the product balloon may be eliminated. On the side of the parison 50 to which the pressurizing member 40 is connected, rotation and positional displacement of the parison 50 are more likely to occur as compared to the side to which the pressurizing member 40 is not connected due to a reaction force at the time of fluid introduction into the lumen 51 of the parison 50. Therefore, the rotation preventing effect of the parison 50 may be further enhanced by providing the rotation preventing portion 20 in either the distal 2-1 section 14 or the proximal 2-1 section 17, the section on the side on which the pressurizing member 40 is connected to the parison 50.

In a case where the fixing member 30 includes the first fixing member 31 for fixing the first side in the longitudinal axis direction x1 of the parison 50, and the second fixing member 35 for fixing the second side in the longitudinal axis direction x1 of the parison 50, and at least any one of the first fixing member 31 and the second fixing member 35 is movable in the longitudinal axis direction x1 of the parison 50, the rotation preventing portion 20 is preferably disposed in any one of the distal 2-1 section 14 and the proximal 2-1 section 17, the section in which either the first fixing member 31 or the second fixing member 35 having a longer distance to move in the longitudinal axis direction x1 of the parison 50 is disposed, the distal 2-2 section 15, and the proximal 2-2 section 18. By providing the rotation preventing portion 20 in the distal 2-2 section 15 and the proximal 2-2 section 18, an influence on the shape and quality of the product balloon may be reduced. On the side in the longitudinal axis direction x1 of the parison 50 on which the fixing member 30 having the longer distance to move is disposed, rotational deviation due to extension of the parison 50 at the time of blow molding is likely to occur as compared to the side on which the fixing member 30 having a shorter distance to move is disposed. Therefore, by providing the rotation preventing portion 20 also in any one of the distal 2-1 section 14 and the proximal 2-1 section 17, the section in which either the first fixing member 31 or the second fixing member 35 having a longer distance to move is disposed, the rotation preventing effect of the parison 50 may be further enhanced.

Hereinafter, a specific aspect of the rotation preventing portion 20 is described.

As illustrated in FIG. 4, it is preferable that the first projection 53 is disposed on the outer surface of the parison 50, and the rotation preventing portion 20 is a first groove 21 disposed on the inner wall surface 19 of the mold 10 and engaging with the first projection 53. As illustrated in FIG. 5, it is preferable that the first projection 53 is disposed on the outer surface of the parison 50, and the rotation preventing portion 20 is a second projection 22 disposed on the inner wall surface 19 of the mold 10 and abutting the first projection 53. The rotation of the parison 50 may be prevented by the engagement between the first projection 53 and the first groove 21 or the abutment between the first projection 53 and the second projection 22.

It is preferable that the first projection 53 extends in the longitudinal axis direction x1 of the parison 50, and the first groove 21 or the second projection 22 extends in the longitudinal direction x2 of the mold 10. By extending the first projection 53 and the first groove 21 or the second projection 22 in this manner, the rotation preventing effect of the parison 50 is enhanced. Note that, in order to prevent positional displacement of the parison 50 in the longitudinal axis direction x1, the first projection 53 may extend in a circumferential direction of the parison 50.

The first projection 53 is preferably disposed at least in a section forming the sleeve outer portion 64 of the balloon 60 of the parison 50, and more preferably disposed in a section forming the sleeve outer portion 64 and the sleeve portion 63 of the balloon 60.

The first projection 53 may be disposed over an entire parison 50 in the longitudinal axis direction x1. In this case, the first groove 21 or the second projection 22 is preferably disposed in the first section 11 and the second section 12 of the mold 10.

One or a plurality of the first projections 53 may be disposed on the outer surface of the parison 50. In order to enhance the rotation preventing effect of the parison 50, it is preferable that a plurality of first projections 53 is disposed apart from each other in a circumferential direction p. FIGS. 4 and 5 illustrate an example in which three first projections 53 extending in the longitudinal axis direction x1 of the parison 50 are disposed at regular intervals in the circumferential direction p.

In a cross-section perpendicular to the longitudinal axis direction x1 of the parison, the first projection 53 may be disposed to be narrowed radially outward. A tip of the first projection 53 may be sharp or rounded.

Although not illustrated, both the first groove 21 engaging with the first projection 53 of the parison 50 and the second projection 22 abutting the first projection 53 may be disposed on the inner wall surface 19 of the mold 10. For example, the first groove 21 may be disposed in any one of the distal second section 13 and the proximal second section 16, and the second projection 22 may be disposed in the other.

A depth of the first groove 21 and a height of the second projection 22 may be the same in the longitudinal direction x2 of the mold 10, or may differ depending on a position in the longitudinal direction x2.

As illustrated in FIG. 6, it is preferable that a first recess 54 is disposed on the outer surface of the parison 50, and the rotation preventing portion 20 is a third projection 23 disposed on the inner wall surface 19 of the mold 10 and engaging with the first recess 54. When the first recess 54 of the parison 50 and the third projection 23 of the mold 10 engage with each other, the rotation of the parison 50 may be prevented.

The first recess 54 preferably extends in the longitudinal axis direction x1 of the parison 50. In this case, the third projection 23 preferably extends in the longitudinal direction x2 of the mold 10. By extending the first recess 54 and the third projection 23 in this manner, the rotation preventing effect of the parison 50 is enhanced.

One or a plurality of the first recesses 54 may be disposed on the outer surface of the parison 50. Similarly, one or a plurality of the third projections 23 may be disposed on the inner wall surface 19 of the mold 10. As for the number and shapes of the first recesses 54 and the third projections 23, a configuration example of the first grooves 21 or the first projections 53 may be referred to.

The parison including the first projection 53 or the first recess 54 may be extrusion molded from a single material or may be molded by co-extrusion using a plurality of materials. The parison including the first projection 53 may be molded by bonding or welding a linear resin mass to a tubular or polygonal tubular resin mass. The parison including the first recess 54 may be molded by cutting out the outer surface of the cylindrical or polygonal tubular resin mass by a method such as cutting or peeling.

The rotation preventing portion 20 is preferably the inner wall surface 19 of the second section 12 of the mold 10 having surface roughness more than surface roughness of the inner wall surface 19 of the first section 11 of the mold 10, or the outer surface of the parison 50 at the position corresponding to the second section 12 having surface roughness more than surface roughness of the outer surface of the parison 50 at a position corresponding to the first section 11. The surface roughness is arithmetic average roughness Ra in a reference length of a roughness curve on the inner wall surface 19 of the mold 10 or the outer surface of the parison 50, and the reference length is 0.1 mm. The rotation of the parison 50 may also be prevented by increasing the surface roughness of the inner wall surface 19 of the mold 10 or the outer surface of the parison 50 in this manner.

The above-described arithmetic average roughness Ra corresponds to the arithmetic average roughness Ra defined in JIS B 0601 (2001), and is measured in accordance with JIS B 0633 (2001). For the measurement, a measuring instrument (for example, a laser microscope VK-9510 manufactured by KEYENCE CORPORATION) defined in JIS B 0651 (2001) is used.

Examples of a method for increasing the surface roughness of the inner wall surface 19 of the mold 10 and the outer surface of the parison 50 include a method for mechanically or chemically roughening these surfaces; there are, for example, a method using etching, blasting, a wire brush, or sandpaper.

The rotation preventing portion 20 is preferably a first frictional resistance member provided on the inner wall surface 19 of the second section 12 and having frictional resistance more than frictional resistance of the inner wall surface 19 of the first section 11, or a second frictional resistance member provided on the outer surface of the parison 50 at the position corresponding to the second section 12 and having frictional resistance more than frictional resistance of the outer surface of the parison 50 at a position corresponding to the first section 11. The rotation of the parison 50 may also be prevented by providing the frictional resistance member on the inner wall surface 19 of the mold 10 or the outer surface of the parison 50 in this manner.

The first frictional resistance member or the second frictional resistance member may be made of an elastic material such as silicone rubber or polyamide-based resin, for example.

The first frictional resistance member or the second frictional resistance member may be disposed in a layered manner, or may be disposed linearly or in a net shape. The first frictional resistance member may extend in at least any one of the longitudinal direction x2 of the mold 10 and the circumferential direction of the parison 50. The second frictional resistance member may extend in at least any one of the longitudinal axis direction x1 of the parison 50 and the circumferential direction of the parison 50. FIG. 7 illustrates an example in which two layered first frictional resistance members 24 are disposed at regular intervals in the circumferential direction, and FIG. 8 illustrates an example in which four linear first frictional resistance members 24 are disposed at regular intervals in the circumferential direction. One first frictional resistance member and one second frictional resistance member may be disposed or a plurality of the first frictional resistance members and a plurality of the second frictional resistance members may be disposed.

Another example of a case where the first projection 53 is disposed on the outer surface of the parison 50 and the rotation preventing portion 20 is the first groove 21 and the second projection 22 of the mold 10 is described with reference to FIGS. 9 to 16. FIG. 9 is a cross-sectional view of the mold 10 according to another embodiment of the present invention, and FIGS. 10 to 16 are cross-sectional views of the mold illustrated in FIG. 9. For example, as illustrated in FIGS. 9 to 11, it is preferable that the first groove 21 is disposed in the proximal 2-2 section 18, and the second projection 22 is disposed in the proximal 2-1 section 17. Accordingly, the tip of the first projection 53 is not easily crushed in the proximal 2-1 section 17, that is, on a side close to the straight tube portion 61 and the tapered portion 62 of the balloon 60.

As illustrated in FIGS. 9 to 11 and FIGS. 15 and 16, it is preferable that the first groove 21 is disposed in the distal 2-2 section 15 and the proximal 2-2 section 18, the second projection 22 is disposed in the proximal 2-1 section 17, and the rotation preventing portion 20 is not disposed in the distal 2-1 section 14. By not disposing the rotation preventing portion 20 in the distal 2-1 section 14 for forming the distal sleeve portion 63D of the balloon 60, the tip of the first projection 53 may be crushed, and slipperiness of the distal sleeve portion 63D of the balloon 60 is appropriately secured, so that crossability of the balloon at the lesion may be enhanced.

In a case where the first groove 21 is disposed in each of the distal 2-2 section 15 and the proximal 2-2 section 18, depths of these grooves may be the same as or different from each other.

A groove or a projection may be disposed separately from the rotation preventing portion 20 on the inner wall surface 19 of the mold 10. For example, as illustrated in FIGS. 12 and 13, a second groove 25 may be disposed on the inner wall surface 19 of the first section 11 of the mold 10. By disposing the second groove 25 in this manner, it is possible to dispose a projection at a position corresponding to the straight tube portion 61 and the tapered portion 62 of the balloon 60 after the parison 50 is expanded.

The step of expanding the parison 50 is described. The parison 50 is expanded by introducing a fluid such as air, nitrogen, or water into the lumen 51 of the parison 50 while heating the parison 50 at glass transition temperature of resin or more. Note that the parison 50 may be extended in the longitudinal axis direction x1 before the step of expanding the parison 50. The step of expanding the parison 50 may be performed only once or a plurality of times. In a case where the step of expanding is performed a plurality of times, it is preferable to use different molds for each expansion.

A step of cutting the parison 50 is described. At the step of cutting the parison 50 at the position corresponding to the second section 12, the parison 50 is preferably cut on a side of the straight tube portion 61 with respect to the portion abutting the rotation preventing portion 20. Accordingly, it is possible to exclude the portion abutting the rotation preventing portion 20 of the parison 50, so that the shape and quality of the product balloon may be easily ensured.

At the step of cutting the parison 50 at the position corresponding to the second section 12, the parison 50 is preferably cut at positions corresponding to the distal second section 13 and the proximal second section 16. The rotation preventing portion 20 is provided in at least any one of the distal second section 13 and the proximal second section 16. By cutting the parison 50 at the positions corresponding to the sections, it is possible to exclude the portion abutting the rotation preventing portion 20 of the parison 50, so that the shape and quality of the product balloon may be easily ensured.

At the step of cutting the parison 50 at the position corresponding to the second section 12, the parison 50 may be cut at a position corresponding to the proximal side with respect to a proximal end of the distal 2-2 section 15 and a position corresponding to the distal side with respect to a distal end of the proximal 2-2 section 18. The parison 50 may also be cut at a position corresponding to a boundary between the distal 2-1 section 14 and the distal 2-2 section 15 and a position corresponding to a boundary between the proximal 2-1 section 17 and the proximal 2-2 section 18.

The parison 50 is preferably cut in the direction perpendicular to the longitudinal axis direction x1, but the parison 50 may also be cut obliquely with respect to the longitudinal axis direction x1.

When cutting the parison 50, a blade such as a knife, a razor, or scissors, or a heat source such as a laser, an ultrasonic wave, or a heater may be used.

The cut parison 50 may be used as the balloon for the balloon catheter. The method for producing the balloon catheter of the present invention preferably further includes a step of fixing the cut parison on the distal side of the shaft.

The shaft includes the distal side and the proximal side. The shaft is usually provided therein with a flow path for the fluid supplied into the balloon and an insertion path for a wire that guides progress of the shaft. For obtaining an excellent fluid flow, the flow path of the fluid preferably extends in a longitudinal direction of the shaft. The shaft may have a coaxial structure formed at least of a double tube, or may have a multi-lumen structure including a plurality of lumens.

The shaft preferably has flexibility. Accordingly, the shaft may be deformed along a body cavity shape. The shaft preferably has elasticity for maintaining a shape thereof. The shaft is preferably made of resin, metal or a combination thereof. For example, the shaft may be a resin tube; a metal tube; a hollow body formed by disposing a single wire or a plurality of wire materials or twisted wire materials in a predetermined pattern; the hollow body at least any one of an inner surface and an outer surface of which is coated with resin; or a combination thereof or that obtained by connecting them in the longitudinal direction.

By using a resin as a component of the shaft, flexibility and elasticity are easily imparted to the shaft. By using metal as a component of the shaft, it is possible to improve deliverability of the balloon catheter. Examples of the resin forming the shaft include a polyamide-based resin, a polyester-based resin, a polyurethane-based resin, a polyolefin-based resin, a fluorine-based resin, a vinyl chloride-based resin, a silicone-based resin, natural rubber, synthetic rubber and the like. It is possible to use only one of them or two or more of them. As the resin forming the shaft, either a thermoplastic resin or a thermosetting resin may be used, and among them, a thermoplastic resin is preferably used. Examples of the metal forming the shaft include stainless steel such as SUS304 and SUS316, platinum, nickel, cobalt, chromium, titanium, tungsten, gold, a Ni—Ti alloy, a Co—Cr alloy, or a combination thereof. Note that the shaft may have a laminated structure made of different materials or the same material.

This application claims the benefit of the priority date of Japanese patent application No. 2019-55202 filed on Mar. 22, 2019. All of the contents of the Japanese patent application No. 2019-55202 filed on Mar. 22, 2019 are incorporated by reference herein.

REFERENCE SIGNS LIST

1: Balloon producing device
10: Mold
10A: First mold
10B: Second mold
10C: Third mold
10D: Fourth mold
10E: Fifth mold
10F: Sixth mold
11: First section
12: Second section
13: Distal second section
14: Distal 2-1 section
15: Distal 2-2 section
16: Proximal second section
17: Proximal 2-1 section
18: Proximal 2-2 section
19: Inner wall surface of the mold
20: Rotation preventing portion
21: First groove
22: Second projection
23: Third projection
24: First frictional resistance member
25: Second groove
30: Fixing member
31: First fixing member
32: Fastening member
33: Teeth
35: Second fixing member
36: Chuck piece
40: Pressurizing member
50: Parison
51: Lumen
53: First projection
54: First recess
60: Balloon
61: Straight tube portion
62: Tapered portion
62D: Distal tapered portion
62P: Proximal tapered portion
63: Sleeve portion
63D: Distal sleeve portion
63P: Proximal sleeve portion
64: Sleeve outer portion
64D: Distal sleeve outer portion
64P: Proximal sleeve outer portion
x1: Longitudinal axis direction of the parison
x2: Longitudinal direction of the mold
p: Circumferential direction of the parison

The invention claimed is:
1. A method for producing a balloon catheter comprising:
preparing a balloon producing device, the device including a mold into which a tubular parison is inserted, and a fixing member for fixing the parison outside the mold, the mold including a first section for forming a straight tube portion and a tapered portion of a balloon, a proximal second section and a distal second section present on both sides of the first section in a longitudinal direction, at least one of the proximal and distal second sections provided with a rotation preventing portion abutting the parison so as to prevent rotation of the tubular parison about a longitudinal axis direction of the parison, the rotation preventing portion configured to form a gap between an inner wall surface of the mold and the parison at a portion where the rotation preventing portion exists in a cross-section perpendicular to the longitudinal direction of the mold;

disposing a part of the parison in the longitudinal axis direction in the mold so that the parison contacts with the rotation preventing portion and the gap is formed between the inner wall surface of the mold and the parison;

fixing a portion disposed outside the mold of the parison with the fixing member;

expanding the parison;

removing the parison from the mold; and cutting the parison at a position corresponding to at least one of the proximal and distal second sections to obtain a balloon catheter, wherein the distal second section is present at a position corresponding to a distal side of the balloon with respect to the first section and the proximal second section is present at a position corresponding to a proximal side of the balloon with respect to the first section such that the first section is located between the proximal second section and the distal second section.

2. The method according to claim 1, wherein the rotation preventing portion is disposed in each of the distal second section and the proximal second section.

3. The method according to claim 1, wherein in the expanding the parison, a pressurizing member for introducing a fluid into the parison is connected to the parison at a proximal side or a distal side in the longitudinal axis direction of the parison and the parison is expanded by introducing the fluid into the parison, and the rotation preventing portion is disposed at the distal second section or the proximal second section, whichever is more adjacent to the pressurizing member, so as to prevent the rotation of the parison.

4. The method according to claim 1, wherein the fixing member includes a first fixing member for fixing a first side in the longitudinal axis direction of the parison, and a second fixing member for fixing a second side in the longitudinal axis direction of the parison, at least one of the first fixing member and the second fixing member is movable in the longitudinal axis direction of the parison so as to extend the parison in the longitudinal axis direction, and the rotation preventing portion is disposed in the distal second section or the proximal second section adjacent to the first fixing member or the second fixing member whichever has a longer distance to move in the longitudinal axis direction of the parison, so as to prevent the rotation of the parison.

5. The method according to claim 1, wherein the fixing member includes a first fixing member for fixing a first side in the longitudinal axis direction of the parison and a second fixing member for fixing a second side in the longitudinal axis direction of the parison, and in the fixing a portion disposed outside the mold of the parison with the fixing member, the first fixing member fixes the first side of the parison such that a lumen cross-sectional shape of the parison is deformed as compared with the shape before fixing, and the second fixing member fixes the second side of the parison such that a deformation amount of the lumen cross- sectional shape of the parison is less than the deformation amount when fixing the parison with the first fixing member.

6. The method according to claim 1, wherein in the cutting the parison at a position corresponding to at least one of the proximal and distal second sections to obtain a balloon catheter, the parison is cut on a side of the straight tube portion with respect to a portion abutting the rotation preventing portion.

7. The method according to claim 1, wherein in the cutting the parison at a position corresponding to at least one of the proximal and distal second sections to obtain a balloon catheter, the parison is cut at positions corresponding to the distal second section second section.

8. The method according to claim 1, wherein a first projection is disposed on an outer surface of the parison, the rotation preventing portion is a first groove disposed on the inner wall surface of the mold to engage with the first projection of the parison, or a second projection disposed on the inner wall surface of the mold to abut the first projection of the parison, and the parison is disposed in the mold so that the first projection of the parison engages with the first groove of the mold or abuts the second projection of the mold.

9. The method according to claim 8, wherein the first projection extends in the longitudinal axis direction of the parison, and the first groove or the second projection extends in the longitudinal direction of the mold.

10. The method according to claim 1, wherein a first recess is disposed on an outer surface of the parison, and the rotation preventing portion is a projection disposed on the inner wall surface of the mold to engage with the first recess, and the parison is disposed in the mold so that the first recess of the parison is engaged with the projection of the mold.

11. The method according to claim 1, wherein the rotation preventing portion is an inner wall surface of at least one of the proximal and distal second sections of the mold having surface roughness more than surface roughness of an inner wall surface of the first section of the mold, or an outer surface of the parison at the position corresponding to at least one of the proximal and distal second sections having surface roughness more than surface roughness of the outer surface of the parison at a position corresponding to the first section, wherein the surface roughness is arithmetic average roughness Ra in a reference length of a roughness curve on the inner wall surface of the mold or the outer surface of the parison, and the reference length is 0.1 mm.

12. The method according to claim 1, wherein the rotation preventing portion is a first frictional resistance member provided on an inner wall surface of at least one of the proximal and distal second sections and having frictional resistance more than frictional resistance of an inner wall surface of the first section, or a second frictional resistance member provided on an outer surface of the parison at the position corresponding to at least one of the proximal and distal second sections and having frictional resistance more than frictional resistance of the outer surface of the parison at a position corresponding to the first section.

13. The method according to claim 1, wherein
the distal second section includes a distal 2-1 section present on a side of the first section for forming a distal sleeve portion of the balloon, and a distal 2-2 section present at a position corresponding to a distal side of the balloon with respect to the distal 2-1 section,
the proximal second section includes a proximal 2-1 section present on a side of the first section for forming a proximal sleeve portion of the balloon, and a proximal 2-2 section present at a position corresponding to a proximal side of the balloon with respect to the proximal 2-1 section, and
the rotation preventing portion is disposed in the distal 2-2 section and the proximal 2-2 section, and at least one of the distal 2-1 section and the proximal 2-1 section.

14. The method according to claim 13, wherein the rotation preventing portion is disposed in the proximal 2-1 section, but is not disposed in the distal 2-1 section.

15. The method according to claim 13, wherein
in the expanding the parison, a pressurizing member for introducing a fluid into the parison is connected to a first side or a second side in the longitudinal axis direction of the parison and the parison is expanded by introducing the fluid into the parison, and
the rotation preventing portion is disposed in the distal 2-1 section or the proximal 2-1 section, whichever is more adjacent to the pressurizing member, so as to prevent the rotation of the parison.

16. The method according to claim 13, wherein
the fixing member includes a first fixing member for fixing a first side in the longitudinal axis direction of the parison, and a second fixing member for fixing a second side in the longitudinal axis direction of the parison,
at least one of the first fixing member and the second fixing member is movable in the longitudinal axis direction of the parison so as to extend the parison in the longitudinal axis direction, and the rotation preventing portion is disposed in the distal 2-1 section or the proximal 2-1 section adjacent to the first fixing member or the second fixing member whichever has a longer distance to move in the longitudinal axis direction of the parison.

* * * * *